United States Patent [19]

Matsumoto et al.

[11] 4,420,640

[45] Dec. 13, 1983

[54] METHOD OF PRODUCING 1,9-NONANEDIAL AND 9-HYDROXY-7-NONEN-1-AL

[75] Inventors: Mitsuo Matsumoto; Noriaki Yoshimura; Masuhiko Tamura, all of Kurashiki, Japan

[73] Assignee: Kuraray Co., Ltd., Kurashiki, Japan

[21] Appl. No.: 372,337

[22] Filed: Apr. 27, 1982

[30] Foreign Application Priority Data

Apr. 30, 1981 [JP] Japan ................................ 56-66367
May 26, 1981 [JP] Japan ................................ 56-80642

[51] Int. Cl.$^3$ ............................................ C07C 45/50
[52] U.S. Cl. .................................... 568/454; 568/448; 568/909; 502/162
[58] Field of Search ............... 568/454, 448, 496, 909; 252/429 R

[56] References Cited

U.S. PATENT DOCUMENTS 4,215,077 7/1980 Matsumoto et al. ................ 568/454
4,275,243 6/1981 Saito et al. ......................... 568/454

*Primary Examiner*—Werren B. Lone
*Attorney, Agent, or Firm*—Oblon, Fisher, Spivak, McClelland & Maier

[57] ABSTRACT

There is disclosed a method of producing 1,9-nonanedial and/or 9-hydroxy-7-nonen-1-ol which comprises reacting 2,7-octadien-1-ol with a mixture of hydrogen and carbon monoxide in an organic solvent in the presence of a rhodium catalyst and 30–300 equivalents of a monodentate tertiary organic phosphorus compound in per gram atom of rhodium at a hydrogen partial pressure of 0.5–20 kg/cm$^2$ (absolute) and a carbon monoxide partial pressure of 0.1–5.0 kg/cm$^2$ (absolute).

6 Claims, No Drawings

METHOD OF PRODUCING 1,9-NONANEDIAL AND 9-HYDROXY-7-NONEN-1-AL

BACKGROUND OF THE INVENTION

1. Field of the Invention

This invention relates to a method of producing 1,9-nonanedial and/or 9-hydroxy-7-nonen-1-al. More particularly, the invention relates to a method of producing 1,9-nonanedial and/or 9-hydroxy-7-nonen-1-al which comprises reacting 2,7-octadien-1-ol with a mixture of hydrogen and carbon monoxide in the presence of a catalyst.

2. Description of the Prior Art 1,9-Nonanedial is useful as a protein- or enzyme-immobilizing agent, a microbicidal agent, or a starting material for the production of industrially valuable compounds such as azelaic acid, 1,9-nonanediol and 1,9-nonanediamine. Prior to the present invention, however, advantageous methods for producing 1,9-nonanedial have not been developed and accordingly 1,9-nonanedial has not yet been produced on a commercial scale. An example of a conceivable process for producing 1,9-nonanedial would comprise subjecting oleic acid to ozonolysis, esterifying the resulting azelaic acid and subjecting the azelaic acid ester to half reduction with lithium aluminum hydride. However, such a process would have such drawbacks as difficulty in selective production of 1,9-nonanedial by half reduction and high costs of starting material and reducing agent, and consequently would be impractical from the commercial viewpoint. A commercially advantageous method for the production of 1,9-nonanedial using an inexpensive starting material has previously been unavailable.

SUMMARY OF THE INVENTION

It has been found that 1,9-nonanedial and/or an isomer thereof, namely 9-hydroxy-7-nonen-1-al, can be produced in good yields by reacting 2,7-octadien-1-ol with a mixture of hydrogen and carbon monoxide in an organic solvent in the presence of a rhodium catalyst and a monodentate tertiary organic phosphorus compound in an amount of 30–300 equivalents per gram atom of rhodium at a hydrogen partial pressure of 0.5–20 kg/cm$^2$ (absolute) and a carbon monoxide partial pressure of 0.1–5.0 kg/cm$^2$ (absolute). The ratio of 9-hydroxy-7-nonen-1-al to 1,9-nonanedial can be varied as desired by selecting appropriate reaction conditions (described later). 9-Hydroxy-7-nonen-1-al provided by the present invention is represented by the formula OHCCH$_2$CH$_2$CH$_2$CH$_2$CH$_2$CH$_2$CH=CHCH$_2$OH and is a novel compound which has not been described in the literature. This compound can easily be converted to 1,9-nonanedial by isomerization or reduced to 1,9-nonanediol. 1,9-Nonanediol is a useful intermediate in the production of polyesters and polyurethanes.

The so-called hydroformylation reaction used in this invention is well known. Thus, when various olefinic compounds are reacted with a mixture of hydrogen and carbon monoxide, the corresponding aldehydes are obtained. Unexpectedly, however, it has now been found that, when 2,7-octadien-1-ol is reacted with a mixture of hydrogen and carbon monoxide under appropriate conditions in accordance with the invention, not only is 9-hydroxy-7-nonen-1-al, the expected product, produced, but an unexpected isomerization product, namely 1,9-nonanedial, is also produced in good yield.

DETAILED DESCRIPTION OF THE INVENTION

As the rhodium catalyst to be used in the practice of the invention, any rhodium complex compound may be used. However, when the catalytic activity, selectivity of reaction, stability of the catalyst and other factors are considered, rhodium cluster complexes, typically Rh$_4$(CO)$_{12}$ and Rh$_6$(CO)$_{16}$ as well as HRh(CO)(PPh$_3$)$_3$ (where PPh$_3$ stands for triphenylphosphine), which can show good catalytic activity under low pressures, are especially preferred. It is also possible to prepare a rhodium complex compound by a conventional method in a catalyst preparation vessel provided separately and feed the catalyst solution as prepared to the reaction vessel. The rhodium catalyst is preferably used at a rhodium concentration of 0.01–10 milligram atoms per liter of the liquid reaction mixture. Possible monodentate tertiary organic phosphorus compounds include a large number of compounds, preferably trisubstituted phosphine and phosphite compounds represented by the general formula PR'R''R''', wherein R', R'' and R''' are the same or different and each is an aryl, aryloxy, alkyl or alkoxy group. Preferred aryl groups are phenyl and naphthyl groups, either unsubstituted or substituted with a lower alkyl or alkoxy group. Preferred alkyl groups are lower alkyl groups containing 1–8 carbon atoms. Examples of such trisubstituted phosphine and phosphite compounds are triphenylphosphine, tritolylphosphine, trinaphthylphosphine, diphenylpropylphosphine, diphenylbutylphosphine, triphenyl phosphite, and the like. Generally, the monodentate tertiary organic phosphorus compound is used at a rate of 30–300 equivalents per gram atom of rhodium. When the amount of the monodentate tertiary organic phosphorus compound is smaller than about 30 equivalents per gram atom of rhodium, the formation of branched aldehydes tends to increase, and the rhodium catalyst tends to become inactivated. Conversely, when the amount of the monodentate tertiary organic phosphorus compound exceeds about 300 equivalents per gram atom of rhodium, the rate of formation of 1,9-nonanedial and/or 9-hydroxy-7-nonen-1-al decreases markedly to an extent as to render the method impractical from a commercial viewpoint.

It is possible to increase the relative proportion of 9-hydroxy-7-nonen-1-al by adding a bidentate diphosphinoalkane to the reaction mixture. When a bidentate diphosphinoalkane of the general formula (I)

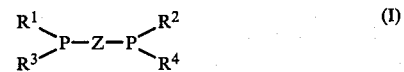

wherein R$^1$ and R$^2$ each is an aryl group, R$^3$ and R$^4$ each is an aryl group or a hydrocarbon group containing at least one carbon atom and Z is an alkylene group, optionally lower alkyl- or alkylene-substituted, containing 2–5 carbon atoms in the straight chain portion thereof, is present in an amount of 0.2–5.0 equivalents per gram atom of rhodium, an increased ratio in yield of 9-hydroxy-7-nonen-1-al to 1,9-nonanedial is attained. In the above-mentioned general formula (I), R$^1$ and R$^2$ each is an aryl group. Preferred aryl groups are 6-membered, monocyclic, hydrocarbyl groups; i.e., phenyl and hydrocarbyl substituted phenyl groups. $R^3$ and $R^4$ each is an aryl group or a non-aryl hydrocarbon group such as a saturated hydrocarbon group (e.g. methyl, ethyl, propyl, butyl, pentyl, hexyl, heptyl, octyl, cyclohexyl). Examples of the alkylene group Z are:

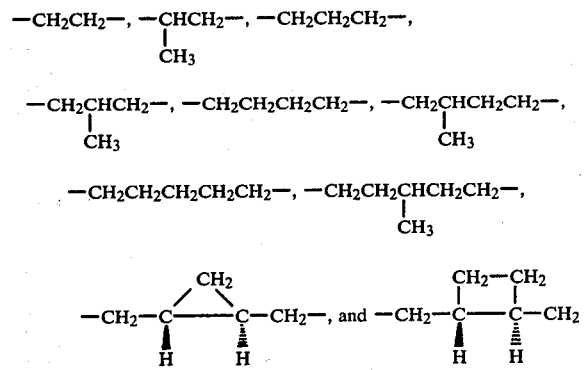

In the above, the formula

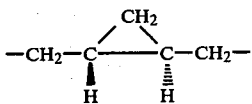

for instance, indicates that the >P—CH$_2$— and —CH$_2$P< groups are arranged trans to each other in the bidentate diphosphinoalkane containing such alkylene group. Preferred examples of the bidentate diphosphinoalkane are: Ph$_2$PCH$_2$CH$_2$PPh$_2$ wherein Ph is a phenyl group,

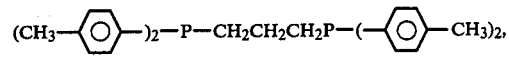

Ph$_2$PCH$_2$CH$_2$CH$_2$CH$_2$PPh$_2$, and

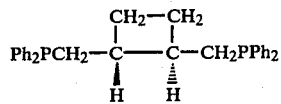

The starting material used in accordance with the invention, 2,7-octadien-1-ol, can easily be prepared on a commercial scale by reacting butadiene with water in the presence of a palladium complex compound as the main catalyst by the method proposed earlier by the present inventors (GB 2,074,156A).

In carrying out the reaction in accordance with the present invention, it is necessary to maintain the hydrogen partial pressure within the reaction system at 0.5–20 kg/cm$^2$ (absolute) and the carbon monoxide partial pressure at 0.1–5.0 kg/cm$^2$ (absolute). When the carbon monoxide partial pressure is lower than about 0.1 kg/cm$^2$ (absolute), hydrogenation and isomerization (displacement of the terminal double bond) take place to an excessive extent. When the carbon monoxide partial pressure exceeds about 5.0 kg/cm$^2$ (absolute), the yields of branched aldehydes and hydroxydialdehydes (products from hydroformylation of the internal double bond) increase. The hydroxydialdehydes are thermally unstable and easily convertible to polycondensation products, causing various difficulties in the reaction step and making it difficult in the distillation step to separate the products. It is therefore desirable to suppress the formation of hydroxydialdehydes as completely as possible. When the hydrogen partial pressure is lower than about 0.5 kg/cm$^2$ (absolute), the reaction does not proceed at a satisfactory rate. When the hydrogen partial pressure exceeds about 20 kg/cm$^2$ (absolute), double bond hydrogenation takes place to a considerable extent. When the hydrogen partial pressure and the carbon monoxide partial pressure are maintained within the above-specified respective ranges, the yield of 1,9-nonanedial increases as the carbon monoxide partial pressure decreases.

A gas inert to the reaction, such as nitrogen, helium, argon, methane, ethane, propane or butane, may optionally be present in the reaction system. The reaction temperature is selected with the ranges of 40°–130° C., preferably 50°–120° C. At a reaction temperature lower than 40° C., the rate of reaction is too slow for the method to be advantageous from a commercial viewpoint. When the reaction temperature exceeds 130° C., undesirable side reactions take place, and the rhodium catalyst tends to become inactivated. As for solvent in which the reaction takes place, the starting material, the product or a condensation product therefrom may serve as a solvent, but any organic solvent inert to the reaction and capable of dissolving the rhodium catalyst and the organic phosphorus compound may also be used. Usable organic solvents include aromatic hydrocarbons, alcohols, ethers and esters, among others. Considering such factors as the solubilities of the rhodium catalyst and the organic phosphorus compound, the thermal stability of the products, and the difference in boiling point between the products and solvent, high-boiling diesters, such as 1,8-octanediol diacetate, 1,10-decanediol diacetate and diocytyl phthalate are preferred as solvents. The reaction can be carried out either continuously or batchwise in a stirring-type reaction vessel, a bubble-tower-type reaction vessel or a packed-column-type reaction vessel.

1,9-Nonanedial and/or 9-hydroxy-7-nonen-1-al can be separated from the liquid reaction mixture by usual distillation procedures. Thermal degradation of rhodium catalyst encountered during distillation may be suppressed by adding an appropriate amount of a disubstituted phosphine oxide to the reaction system in accordance with an earlier proposal by the present inventors (U.S. Pat. No. 4,238,419).

1,9-Nonanedial can be converted by oxidation to azelaic acid which is commercially useful as a raw material for the production of lubricants, polyesters and plasticizers, among others. 1,9-Nonanedial can also be converted by hydrogenation to 1,9-nonanediol which is useful as a raw material for the production of polyesters and polyurethanes, for instance. Furthermore, 1,9-nonanedial can be converted to 1,9-nonanediamine by reaction with ammonia and hydrogen. On the other hand, 9-hydroxy-7-nonen-1-al can easily be converted to 1,9-nonanedial by isomerization in the presence of a catalyst such as a copper- or chromium-containing catalyst or to 1,9-nonanediol by hydrogenation.

Having now generally described this invention, the same will be better understood by reference to certain specific examples, which are included herein for purposes of illustration only are not intended to be limiting of the invention or any embodiment thereof, unless specified.

EXAMPLE 1

A one-liter, four-necked flask equipped with thermometer, stirrer, reflux condenser and gas inlet was charged with a solution of 0.50 millimole of HRh(CO)(PPh$_3$)$_3$ and 50 millimoles of PPh$_3$ (triphenylphosphine) in 400 ml of dioctyl phthalate. The flask was purged with nitrogen gas and then filled with a hydrogen-carbon monoxide mixture (mole ratio 3:1) and thereafter heated to a constant temperature of 85° C. (inside temperature). Then 94.5 g (0.75 mole) of 2,7-octadien-1-ol was added continuously with stirring over 2 hours by means of a metering pump while passing through the flask contents a mixed gas composed of hydrogen and carbon monoxide (mole ratio 3:1; hydrogen partial pressure 0.75 kg/cm$^2$ (absolute); carbon monoxide partial pressure 0.25 kg/cm$^2$ (absolute)) at the rate of 10 liters per hour. Thereafter stirring was continued for an additional hour. After carrying out the reaction in this manner for 3 hours, the liquid reaction mixture was analyzed by gas chromatography; the conversion of 2,7-octadien-1-ol was 87%, and the selectivities toward 1,9-nonanedial and 9-hydroxy-7-nonen-1-al were 43% and 40%, respectively. Other products found were 9-hydroxy-6-nonen-1-al and 8-hydroxy-2-methyl-6-octen-1-al with selectivities of 5.0% and 4.0%, respectively as well as 2-methyl-1,8-octanedial, 2,6-octadien-1-ol and n-octanol, each in a trace amount.

Upon distillation of the liquid reaction mixture under reduced pressure, 1,9-nonanedial first distilled out at 74°–75° C. under about 0.5 mmHg (absolute), and then 9-hydroxy-7-nonen-1-al followed at 88°–89° C. under the same pressure. The $^1$H-NMR spectrum of 9-hydroxy-7-nonen-1-al in CDCl$_3$ gave the following δ values (standard: hexamethyldisiloxane):

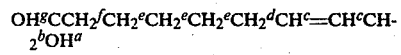

H$^a$: 2.73(1H, s), H$^b$: 4.02(2H, d),
H$^c$: 5.60(2H, m), H$^d$: 2.01(2H, q),
H$^e$: 1.30–1.68(6H, m), H$^f$: 2.38(2H,td),
H$^g$: 9.73(1H,t)

The IR spectrum showed strong absorptions at 3,400 cm$^{-1}$, 2,926 cm$^{-1}$, 2,857 cm$^{-1}$ and 1,721 cm$^{-1}$.

EXAMPLE 2

A one-liter stainless steel autoclave equipped with thermometer, magnetic stirrer, reflux condenser and gas inlet was charged with a solution of 0.25 millimole of Rh$_4$(CO)$_{12}$ and 150 millimoles of triphenylphosphine in 450 ml of 1,10-decanediol diacetate. The autoclave was purged with nitrogen gas and then filled with a hydrogen-carbon monoxide mixture (mole ratio 5:1) and heated to a constant temperature of 80° C. (inside temperature). Thereafter 63 g (0.50 mole) of 2,7-octadien-1-ol was added to the autoclave, and then a hydrogen-carbon monoxide mixture (mole ratio 5:1) was introduced into the autoclave. While maintaining the pressure within the autoclave at 6.0 kg/cm$^2$ (absolute) (carbon monoxide partial pressure 1.0 kg/cm$^2$; hydrogen partial pressure 5.0 kg/cm$^2$) and the discharge gas flow rate at 10 liters per hour, stirring was started. After 2 hours of stirring under the above conditions, the stirring was discontinued. Gas chromatography of the liquid reaction mixture revealed that the conversion of 2,7-octadien-1-ol was 93%, and the selectivities toward 1,9-nonanedial and 9-hydroxy-7-nonen-1-al were 28% and 52%, respectively.

EXAMPLE 3

The same reactor as used in Example 1 was charged with a solution of 0.50 millimole of HRh(CO)(PPh$_3$)$_3$ and 75 millimoles of triphenylphosphine in 450 ml of toluene, purged with nitrogen gas and then with a hydrogen-carbon monoxide mixture (mole ratio: 3:1), and heated to and maintained at 85° C. (inside temperature). The flask was then charged with 31.5 g (0.25 mole) of 2,7-octadien-1-ol, and stirring was started while passing a hydrogen-carbon monoxide mixture (mole ratio 3:1) through the reactor at the rate of 10 liters per hour. After an hour, a very small amount of the liquid reaction mixture was taken out and analyzed by gas chromatography. The conversion of 2,7-octadien-1-ol was 82%, and the selectivities toward 1,9-nonanedial and 9-hydroxy-7-nonen-1-al were 12% and 76%, respectively. Stirring was continued for an additional 2 hours. (Thus stirring lasted for 3 hours in total.) The liquid reaction mixture was analyzed, and it was found that the conversion of 2,7-octadien-1-ol was 97% and the selectivities toward 1,9-nonanedial and 9-hydroxy-7-nonen-1-al were 32% and 51%, respectively.

EXAMPLE 4

The same reactor as used in Example 1 was charged with 0.50 millimole of HRh(CO)(PPh$_3$)$_3$, 50 millimoles of PPh$_3$ and 0.375 millimole of 1,4-bis(diphenylphosphino)butane. The reactor was purged with nitrogen gas, then charged with 450 ml of dioctyl phthalate, purged with a hydrogen-carbon monoxide mixture (mole ratio 3:1) and heated to and maintained at 80° C. Then, while passing a hydrogen-carbon monoxide mixture (mole ratio 3:1) through the reactor at the rate of 20 liters per hour with vigorous stirring, 63.0 g (0.50 mole) of 2,7-octadien-1-ol was fed continuously into the reactor over 30 minutes by means of a metering pump. After completion of the addition, stirring was continued for a further hour. After an overall reaction time of 1.5 hours, the reaction mixture was analyzed by gas chromatography. The conversion of 2,7-octadien-1-ol was 80% and the selectivities toward 1,9-nonanedial and 9-hydroxy-7-nonen-1-al were 18% and 76%, respectively. 8-Hydroxyl-2-methyl-6-octen-1-al was the main by-product.

EXAMPLE 5

The same reactor as used in Example 2 was charged with a solution of 0.125 millimole of Rh$_4$(CO)$_{12}$ and 75 millimoles of triphenylphosphine in 450 ml of toluene, purged with a hydrogen-carbon monoxide mixture (mole ratio 5:1) to a sufficient extent, and heated to and maintained at 85° C. (inside temperature). Then 63.0 g (0.50 mole) of 2,7-octadien-1-ol was fed into the reactor. The same hydrogen-carbon monoxide mixture was introduced into the autoclave so as to adjust the pressure within the autoclave to 4.0 kg/cm$^2$ (absolute) (carbon monoxide partial pressure 0.67 kg/cm$^2$; hydrogen partial pressure 3.33 kg/cm$^2$), the discharge gas flow rate was adjusted to 20 liters per hour, and stirring was started. After 45 minutes, stirring was discontinued, and the liquid reaction mixture was taken out of the autoclave and analyzed by gas chromatography. The conversion of 2,7-octadien-1-ol was 63%, and the selectivities toward 1,9-nonanedial and 9-hydroxy-7-nonen-1-al were 28% and 64%, respectively.

COMPARATIVE EXAMPLE 1

The procedure of Example 2 was followed except that the hydrogen-carbon monoxide mixture had a mole ratio of 2:1 and the reaction pressure was 45 kg/cm$^2$ (absolute) (carbon monoxide partial pressure 15 kg/cm$^2$; hydrogen partial pressure 30 kg/cm$^2$). Gas chromatography of the liquid reaction mixture showed that the conversion of 2,7-octadien-1-ol was 99% but that the selectivities toward 1,9-nonanedial and 9-hydroxy-7-nonen-1-al were only 28% and 16%, respectively. When the liquid reaction mixture was allowed to stand, a white polymeric material precipitated on the bottom.

COMPARATIVE EXAMPLE 2

The procedure of Example 1 was repeated except that the amount of PPh$_3$ was 5 millimoles. Analysis of the liquid reaction mixture revealed that the selectivities toward 1,9-nonanedial and 9-hydroxy-7-nonen-1-al were only 31% and 8%, respectively. The liquid reaction mixture, which at first had a yellow color, turned brown during the reaction.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method of producing 1,9-nonanedial which comprises reacting 2,7-octadien-1-ol with a mixture of hydrogen and carbon monoxide in an organic solvent in the presence of a rhodium catalyst and 30–300 equivalents of a monodentate tertiary organic phosphorus compound per gram atom of rhodium at a hydrogen partial pressure of 0.5–20 kg/cm$^2$ (absolute) and a carbon monoxide partial pressure of 0.1–5.0 kg/cm$^2$ (absolute), wherein said reacting is carried out at a temperature of 40°–130° C.

2. The method of claim 1, wherein the rhodium catalyst is used at a rhodium concentration of 0.01–10 milligram atoms per liter of the liquid reaction mixture.

3. The method of claim 1, wherein the monodentate tertiary organic phosphorus compound is a trisubstituted phosphine or phosphite of the general formula

PR'R''R''' wherein R', R'' and R''' are the same or different and each is an aryl, aryloxy, alkyl or alkoxy group.

4. The method of claims 1–3, wherein 9-hydroxy-7-nonen-1-al is additionally produced.

5. The method of claim 4, wherein said reaction occurs in the presence of a bidentate diphosphinoalkane of the formula

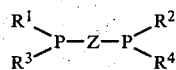

wherein R$^1$ and R$^2$ independently represent an aryl group, R$^3$ and R$^4$ independently represent an aryl group or a hydrocarbon group containing at least one carbon atom and Z represents a linear alkylene group containing 2 to 5 carbon atoms wherein said alkylene group is unsubstituted or is substituted with a lower alkyl or alkylene group.

6. The method of claim 5 wherein Z is a radical selected from the group consisting of

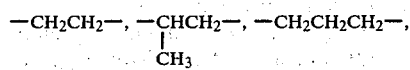

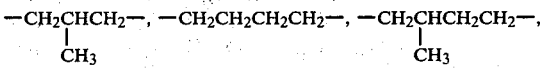

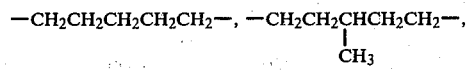

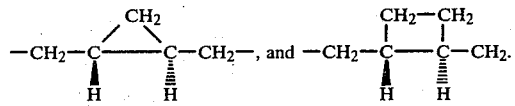

* * * * *